United States Patent [19]

Forssmann et al.

[11] Patent Number: 4,622,969

[45] Date of Patent: Nov. 18, 1986

[54] SHOCK WAVE MATCHING IN THERAPEUTIC EQUIPMENT

[75] Inventors: Bernd Forssmann, Friedrichshafen; Christian Chaussy, Germering, both of Fed. Rep. of Germany

[73] Assignee: Dornier System GmbH, Friedrichshafen, Fed. Rep. of Germany

[21] Appl. No.: 617,750

[22] Filed: Jun. 6, 1984

[51] Int. Cl.[4] .......... A61B 17/22

[52] U.S. Cl. .......... 128/328

[58] Field of Search .......... 128/328, 24 A, 660; 73/642, 644

[56] References Cited

U.S. PATENT DOCUMENTS

| | | | |
|---|---|---|---|
| 3,269,173 | 8/1966 | von Ardenne | 128/24 A |
| 4,003,383 | 1/1977 | Bruck | 128/24 A |
| 4,137,777 | 2/1979 | Haverl et al. | 128/660 X |
| 4,181,120 | 1/1980 | Kunii et al. | 128/660 |
| 4,246,791 | 1/1981 | Glenn | 128/660 X |
| 4,311,147 | 1/1982 | Hausler | 128/328 |

FOREIGN PATENT DOCUMENTS

| | | | |
|---|---|---|---|
| 2913251 | 10/1980 | Fed. Rep. of Germany | 128/328 |

*Primary Examiner*—Michael H. Thaler

*Attorney, Agent, or Firm*—Ralf H. Siegemund

[57] ABSTRACT

An apparatus for the comminution of concrements such as kidney stones, and including a source of shock waves partially surrounded by an ellipsoidal reflector, is improved in that the open end of the reflector for sound wave transmission is additionally defined by a plurality of sound attentuating rings diminishing in internal diameter with distance from the source of shock waves; additional features provide for an overall increase in specific weight of these rings; the transmission of x-rays through the equipment is separately controlled.

12 Claims, 4 Drawing Figures

SHOCK WAVE MATCHING IN THERAPEUTIC EQUIPMENT

BACKGROUND OF THE INVENTION

The present invention relates to the matching of shock waves to particular conditions inherent in a human being, the shock waves being provided for the destruction (comminution) of concrements within the body of such human being, and more particularly the invention relates to the matching of the production and transmission of such a shock waves into the body of a child.

A variety of publications, patents and patent applications deal with devices and methods for contactless comminution of concrements in bodies of human beings by means of ultrasonic shock waves; the method and equipment having been developed by the assignee corporation. Generally speaking, these known equipments include a pan, the bottom of which is configured as or contains an ellipsoidal reflector for sound and ultrasonic waves. An ellipsoid has two focal points, and the arrangment is configured so that in one of these focal points a spark gap produces a shock wave to be refocused and effective in the other focal point upon proper positioning of the equipment vis-a-vis a concrement to be destroyed shock waves can indeed be concentrated such that a concrement being situated in the second focal point will disentegrate. The shock wave fronts are therefore focused by the ellipsoidal reflector into the second focal point, whereby particularly a precise position of the point of origin of the shock wave in one of the focal points ensures that the shock waves are reconcentrated in a geometrically well defined second focal area.

The positioning of the equipment vis-a-vis the concrement to be destroyed will therefore involve positioning of the equipment such that the concrement is in fact situated in that second focal point. The patient will be situated in relation to the pan so that indeed the concrement has the proper position for destruction. The destruction and walls, particularly the kidney stones.

The comminution as such is such that wave fronts of the shock wave impacting upon the concrement near the aforementioned second focal point will cause a portion or a kidney stone, to be ablated and split off a core, ultimately resulting in the total destruction of the stone to the extent that it is reduced to a plurality of relatively small parts which can be past through the urinary tract out of the body system without requiring operative procedure.

It should be noted, however, that the equipment as it was developed, and as it has been practiced, with significant success has been designed for treating adults because the problem of kidney stones is primarily a problem that arises in adults. However, this is not exclusively true. Children may also develop kidney stones, and it was found that the application of the equipment to minors involves certain problems. This involves basically the fact that the dimensions of body parts of a child are smaller in general so that the same equipment cannot be truly "focused" to the kidney stone within the body of a child in quite the same way focusing is permitted with respect to adults simply by external positioning of the reflecting and shock wave generating equipment. Moreover, it was found that particularly in the case of small children the lung may in fact be traversed by not quite but nearly concentrated shock waves or the lung may be affected by certain stray components of the shock wave field. This of course poses an intolerable situation.

DESCRIPTION OF THE INVENTION

It is an object of the present invention to provide a new and improved method and equipment for matching the generation of kidney stone and other concrement comminutions shock wave fields to the unique physiology of children.

It is a particular object of the present invention to provide new and improved method and equipment for the generation of a concrement destroying shock wave field such that organs within the body of a child being fairly close to the concrement to be destroyed will not be adversely affected by the procedure, whereby, however, the principles of kidney stone and other concrement destruction through comminution of a concrement-destroying shock waves is not deviated from.

In accordance with the preferred embodiment of the present invention it is suggested to provide a reflector for shock waves having an ellipsoidal reflecting surface with rotational symmetry on the long axis, but having an opening which is limited through a plurality of exchangeable concentrically arranged annuli or rings made of a material which offers significant impedance against the propagation and transmission of sound waves. While in principle a single ring may suffice using a plurality as stated is preferred, and these rings should have diminishing diameter as far as the interior opening is concerned with distance from the focal point in which the shock waves are produced. Moreover, it was found that these rings should have a cross-section of parrallelepiped like contour, but a rectangular cross-section is also suitable. It was found moreover that these annuli should have a higher specific weight than water or supplemental features should be provided to increase their weight. The rings or annuli should be provided from soft or semi-rigid foam which in fact operates as a sound attenuating and sound absorbing material. Supplemental havy rings e.g. made of lead increase the specific weight of the ring assembly. The phenomenon of parasitic reflection is important because reflection of any sound wave from surfaces or boundaries of these components may occur back into the reflector cavity for further, unfocussed dissipation or absorption. It is moreover suggested to provide annuli in a configuration that is self-centering. In furtherance of the invention it may be advisable to provide these annuli or rings with notches for accommodating additional equipment. It was found and will be explained more fully below that it is of advantage to provide the annuli, at least to some extent, of such a material and in such a configuration that x-rays can pass through them with no or little attenuation.

The entire equipment should be embedded within a jacket or coating of foam so as to provide external noise extenuation. The annuli should have rectangular or oval openings which, as stated, should reduce in overall area with distance from the reflector and the focal point in which the shock waves are generated.

The inventive features as outlined above permit readily an individual matching of the shock wave energy to the overall size of the patient involved. This involves particularly the area that is being affected by the shock waves. The annuli or rings should be made easily exchangeable simply for adapting the equipment to different sized patients. Each of these annuli should be constructed for self-centering operation so that the adaptation procedure of the equipment to different size patients does not involve complicated adjusting procedure.

Annuli and rings of different size should be concentrically arranged with respect to each other, and this way a particularly selected stack of rings permits exact accommodation to the desired opening of the reflector and the thickness of the overall configuration. Upon appropriately dimensioning the rings as stated, the shock wave field is in fact limited or restricted by attenuating edge zones of the transmitting lobes. This is a very important feature because the various rings as stacked will thus avoid that a small patient accidentally is disposed too close to the ellipsoid as such so that in turn too large a portion of his body is subjected to the shock waves. Even though the shock waves remain unfocused outside of the second focal area, a large shock wave field penetrating into the body of a patient may even if unfocused have detrimental physiological effects. Therefore, the invention permits matching of the equipment to the body size of the patient in the sense that the amount of shock wave energy that traverses any portion of the body of a patient is minimized and restricted to that amount necessary for the destruction of a kidney stone or the like. The rigid connection of these diaphragm-like rings with a reflector is effective only to eliminate side lobe portions of the shock wave field, and will never affect the central portion of the shock waves. In other words, the matching equipment as proposed here will under no circumstances interfere with the principle operation of kidney stone and other concrement destruction.

DESCRIPTION OF THE DRAWINGS

While the specification concludes with claims particularly pointing out and distinctly claiming the subject matter which is regarded as the invention, it is believed that the invention, the objects and features of the invention, and further objects, features and advantages thereof will be better understood from the following description taken in connection with the accompanying drawings in which:

Proceeding now to the detailed description of the drawings, FIG. 1 illustrates, broadly speaking, a portion of the body 6 of a human being partially inserted in a pan 2 filled with liquid such as water. The bottom of this pan is extended by an ellipsoidal or truncated ellipsoidal portion type reflector 4. Reference numeral 16 denotes one of the two focal points of this ellipsoid 4. The ellipsoid of course has a second focal point which is idientified by reference numeral 8, and it is assumed in this incidence that a concrement, for example a kidney stone, is situated in that location.

Figure 1:
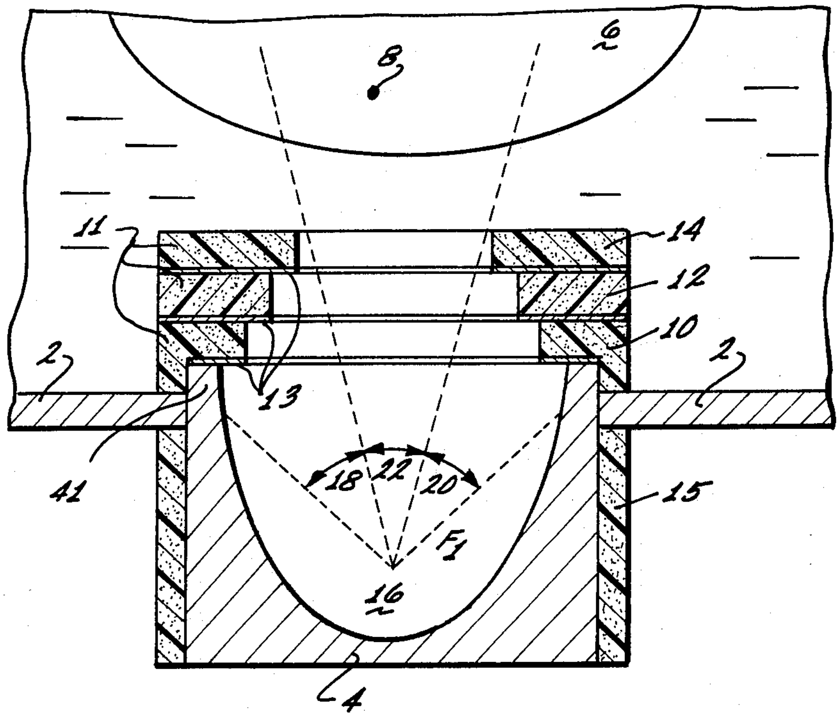
FIG. 1 is a cross-section through a matched piece of equipment for the destruction of concrements in the body of a human being such that a child and being improved in accordance with the preferred embodiment of the present invention for practicing the best mode thereof.

The inventive equipment includes furthermore a staggered diaphragm system being comprised of concentric annuli or rings 10, 12 and 14. These rings are made of an accoustically attenuating and/or reflecting material. In the preferred form, they are made of a foam material. The lowest ring 10 has a cylindrical extension abutting against the flange 2. This lowest ring 10 is moreover centered by the edge 41 of the reflector body 4 as it extends into this cylindrical extension of the ring 10.

The rings 12 and 14 are stacked on top of the ring 10. Each of these rings has a rectangular cross-section. Ring 12 has an inner diameter smaller than the inner diameter or ring 10, and the ring 12 has an inner diameter smaller than the inner diameter of ring 12. The openings of the rings would be circular, oval or even rectangular. The rings are preferably made of foam as stated, and the pores or cells of the foam may simply contain air. It was furthermore found to be of advantage to separate the rings 10, 12 and 14 by means of lead foils 13 being of an annular configuration and having an inner diameter, respectively, equal to the inner diameter of the respective ring above. This feature prevents the arrangement and particularly the rings from floating because it increases the specific weight of the assembly as a whole.

The reflector body 4 moreover is encased in a cylindrical foam jacket 15, which may, but does not have to, consist of the same foam material used for the rings 10, 12 and 14. This foam jacket 15 provides a reduction in the noise that can emanate from the system whenever a spark discharges in focal point 16.

In order to destroy and comminuate a concrement, such as a kidney stone in focal point 8, a spark is generated in the focal point 16. Generation of such a spark is for example of the type disclosed in U.S. Pat. No. 3,942,531. Whenever such a spark occurs, a shock wave is produced which propagates radially outwardly from that focal point in a spherical fashion as far as the wave fronts are concerned. The wave portion that is reflected towards the surface of reflector 4 will upon impact be reflected and in fact refocused into the focal point 8 to thereby destroy any concrement situated in that point.

Reference numerals 18 and 20 in fact define a conical sector or zone into which a certain portion of the shock wave energy is transmitted. These shock wave portions do not participate in the destruction of the concrement in focal point 8 simply because they are not being focused. It can be seen that the zone 18–20 is not terminated directly at the edge of the ellipsoidal reflector surface because of the overhung portion of the lowest ring 10. A certain portion of the shock wave energy within the zones 18 and 20 will be reflected by the reflector surface 4, but will reach this ring 10, thus locking off or shielding a certain portion of the reflector surface. This has the specific purpose of controlling better any edge effect and stray field particulars to make sure that shock wave energy that will reach the body of the patient remains unfocused or will become properly focused in point 8 and not elsewhere. Therefore, stray field portions of the shock waves are absorbed accoustically within the diaphragm system as established by the rings. The staggered relationship provides for a series of effectiveness concerning the absorption so that any edge effect of shock waves and stray fields produced by edges closer to the focal point 16 will be absorbed by rings farther away from the focal point 16.

It can thus be seen that the diaphragm system as provided by the inventive arrangement avoids residual and parasitic side effects by the shock waves as they propagate into the body of the patient. Aside from these various stray components of the shock wave fields resulting from the finite dimensions of the reflector system there are other stray components due to the finite dimensions of the spark gap in the generating zone near the focal point 16, and these stray components are likewise attenuated.

Through appropriate selection of diaphragm-like shock wave attenuating rings, one ultimately selects an effective cone 22 which defines the opening through which unattenuated shock waves can propagate directly from the focal area 16. These directly transmitted shock waves are of course not focused and their energy content and in total intensity should be minimized. Moreover, the selection of this cone permits a delineation of a range for such shock waves such that any vital or particularly sensitive organs will not be situated within that cone and within the propagation path of shock waves that propagate within that cone.

Experiments have shown that the reduction of the effective reflector surface as a result of the inventive procedure, particularly the shading of edge zone can indeed be tolerated. This is particularly true in cases where the equipment is applied for the destruction of kidney stone in a child because the overall transmission path length of any waves into the body of a child is short to begin with. This means that any shock wave attenuation by the body of the patient itself is minimized in such a case. On the other hand, it will be realized that the shock wave energy as produced depends upon the intensity of the spark that is being generated for purposes of generating the shock waves, and control here permits supplemental adaptation of the operating parameters to the permanent conditions.

Figure 2:
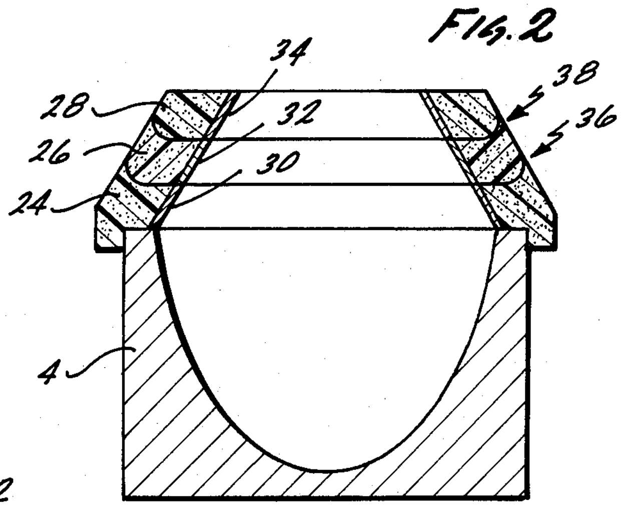
FIG. 2 illustrates a modifiction provided for reasons which will become more apparent pursuant to the detailed description of the drawing.

FIG. 2 illustrates a modification of the shock wave attenuating system as per the invention, whereby the overall contour of the components involved is selected such that there are little or no losses in edge zones. This then requires the rings, such as 24, 26 and 28, to have a internal surface contour that can at least be considered to be a first order approximation of an ellipsoid. This in turn means that the rings in overall configuration should have a near prallelepiped like cross-section. It is particularly important to provide the internal surfaces of each of the rings such that the surfaces 32 and 34 are in fact situated on a common cone and therefore transitionless merge into each other as far as overall effective reflecting surface is concerned. The effective reflector surface as far as body 4 is concerned is not being diminished in this manner, i.e., shading is minimized simply because there is less to be shaded.

In order to provide not only of a centering of the ring closest to the reflector body, which in this case is ring 24 whose centering is being provided by a cylindrical extension, one contours the axial surfaces of these rings such to have a uplifted-like outer portion such as 36 and 38, whereby, as can be seen from the drawings, the placement of the rings permits a kind of self-centering nested disposition.

Figure 3:
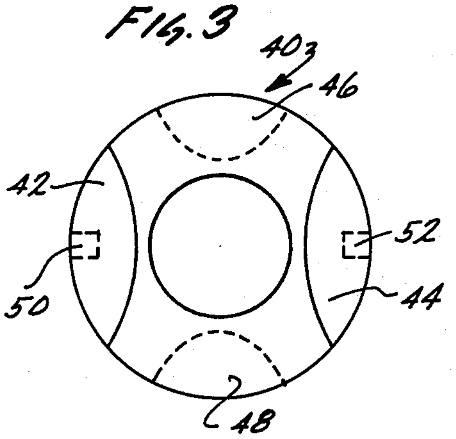
FIG. 3 shows a planned view of one of the annuli used in any of the equipment shown in FIGS. 1 and 2.

FIG. 3 illustrates in elevational view a ring whose outer and inner periphery is still circular, but which from an overall point of view does not have a rotational symmetry. The ring 40, which can be any of the rings 10, 12, 14, 26 and 28 in the previously described examples, has on its upper side two cutouts 42 and 44 which provide space for locating equipment such as x-ray equipment or transmission paths for x-rays. In order to avoid any impediment in the transmission of x-rays, ring 40 will be bounded by lead surfaces such as 46 and 48 in limited zones only.

The foam to be used for any of the rings is selected primarily for purposes of establishing a very high acoustic impedance. Generally speaking, little or no absorption for x-rays will be provided by such a material. The lower side of the ring as shown in FIG. 3 is provided with pins or projections 50 and 52 to engage corresponding cutouts or bores in the respective ring below. This then is another feature for centering the rings with respect to each other, whereby the asymmetry of the centering equipment establishes in addition a security against turning. This is important because the azimuthal disposition of lead and cutout is important in this instance.

Figure 4:
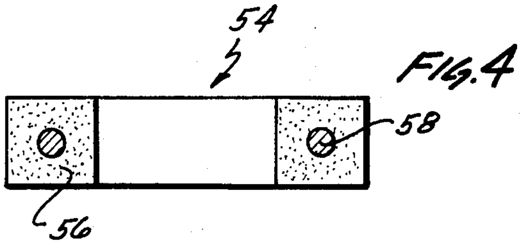
FIG. 4 illustrates a cross-section through a single ring used in the equipment shown in FIG. 1, but with inclusion of a supplemental feature.

FIG. 4 illustrates a cross-section through another example for any of the rings. The ring is shown to have a rectangular cross-section, but other cross-sections within the purview of the preceding disclosures is readily feasible. The ring shown here is provided of a foam body 56 of the type and material mentioned above, but in order to avoid an undue floating effect alluded to above, a metal ring 58 is inserted to increase the overall specific weight of the ring.

The invention is not limited to the embodiments described above, but all changes and modifications thereof not constituting departures from the spirit and scope of the invention are intended to be included.

We claim:

1. In an apparatus for the comminution of concrements in the body of a human being which includes a source for shock waves situated in a first focal point of an ellipsoidal reflector, the apparatus to be positioned such that a second focal point of said reflector is located in the concrement to be destroyed, the improvement of a structure for matching the shock wave field produced upon production of a shock wave in the firstmentioned focal point to the body of the patient, particularly the body of a child, comprising:

said reflector having a particular opening; and an assembly which includes a plurality of concentric shock wave attenuating exchangeable rings made of foam and being removably placed at said opening and in superimposing relationship and having inner openings that decrease with axial distance of the rings from the first focal point,said rings providing restriction for shock wave emanation from the opening of the reflector and as now defined by the openings of the rings, said assembly further including a means for weight increasing, having a specific weight so that the assembly of foam rings as a whole have a specific weight larger than the specific weight of water.

2. The improvement as in claim 1, said rings having rectangular cross-sections.

3. The improvement as in claim 2, said rectangular cross-sections having increasing long rectangular sides respectively with distance from said first-mentioned focal point.

4. The improvement as in claim 1, said rings having a parallelepiped like cross-sections.

5. The improvement as in claim 1, said parallelepiped like cross-sections together defining a conical internal surfaces such that said internal conical surfaces are all situated on a common cone.

6. The improvement as in claim 1, there being weight increasing annuli interposed between said rings.

7. Improvement as in claim 1, including means for centering the rings with respect to each other.

8. Improvement as in claim 1, including an axial extension of said ring to obtain self-centering positioning with respect to said reflector.

9. The improvement as in claim 1, said ring including at least one cutout for accommodating additional equipment.

10. The improvement as in claim 1, wherein means are provided for at least partially blocking x-ray transmission through the ring.

11. The improvement as in claim 1, said reflector being enveloped in a jacket of sound attenuating material.

12. The improvement as in claim 1, wherein said ring has an internal contour being non-circular.

* * * * *